(12) United States Patent
Young

(10) Patent No.: US 8,027,906 B2
(45) Date of Patent: Sep. 27, 2011

(54) PORTRAYAL OF HUMAN INFORMATION VISUALIZATION

(75) Inventor: Charles Young, Albuquerque, NM (US)

(73) Assignee: Hello-Hello, Inc., Albuquerque, NM (US)

( * ) Notice: Subject to any disclaimer, the term of this patent is extended or adjusted under 35 U.S.C. 154(b) by 444 days.

(21) Appl. No.: 11/623,722

(22) Filed: Jan. 16, 2007

(65) Prior Publication Data

US 2007/0197933 A1   Aug. 23, 2007

Related U.S. Application Data

(63) Continuation of application No. 09/517,195, filed on Mar. 2, 2000, now Pat. No. 7,169,113, which is a continuation of application No. PCT/US98/18434, filed on Sep. 4, 1998.

(60) Provisional application No. 60/057,973, filed on Sep. 5, 1997.

(51) Int. Cl.
*G06F 21/00* (2006.01)

(52) U.S. Cl. .......... 705/37; 705/1.1; 705/14.4; 345/419; 345/421; 345/422; 345/473; 348/42; 348/47; 348/51; 348/589; 348/468; 348/565; 348/569; 359/23

(58) Field of Classification Search ....... 705/37
See application file for complete search history.

(56) References Cited

U.S. PATENT DOCUMENTS

| | | | |
|---|---|---|---|
| 4,646,145 A | 2/1987 | Percy et al. | |
| 4,647,964 A | 3/1987 | Weinblatt | |
| 4,861,154 A | 8/1989 | Sherwin et al. | |
| 4,931,865 A | 6/1990 | Scarampi | |
| 5,052,401 A | 10/1991 | Sherwin | |
| 5,220,501 A | 6/1993 | Lawlor et al. | |
| 5,227,874 A | 7/1993 | Von Kohorn | |
| 5,331,969 A | 7/1994 | Silberstein | |
| 5,424,945 A | 6/1995 | Bell | |
| 5,465,729 A | 11/1995 | Bittman et al. | |
| 5,544,354 A | 8/1996 | May et al. | |
| 5,676,138 A | 10/1997 | Zawilinski | |
| 5,731,805 A | 3/1998 | Tognazzini et al. | |
| 6,011,578 A | 1/2000 | Shatto et al. | |
| 6,088,030 A | 7/2000 | Bertram et al. | |

(Continued)

FOREIGN PATENT DOCUMENTS

KR   2002-0067759   *   2/2002

(Continued)

OTHER PUBLICATIONS

Young et al. Guideline: Tracking The Commercial Viewer's Wandering Attention (Jun./Jul. 1987). Retrieved from the IDS.*

(Continued)

*Primary Examiner* — James A Reagan
(74) *Attorney, Agent, or Firm* — Philip D. Askenazy; Deborah A. Peacock; Peacock Myers, P.C.

(57) ABSTRACT

An apparatus and method for displaying viewer reactions to a display object. The display object is divided into a plurality of spatial regions, viewer reactions are collected to an exposure to the display object and correlated with the spatial regions, and the display object is displayed with an aspect of the display of each spatial region being a function of the viewer reactions for the region.

11 Claims, 5 Drawing Sheets

U.S. PATENT DOCUMENTS

| | | | |
|---|---|---|---|
| 6,118,427 | A | 9/2000 | Buxton et al. |
| 6,322,368 | B1 | 11/2001 | Young et al. |
| 6,502,076 | B1 | 12/2002 | Smith |
| 6,519,571 | B1 | 2/2003 | Guheen et al. |
| 6,839,680 | B1 | 1/2005 | Liu et al. |
| 6,868,525 | B1 | 3/2005 | Szabo |
| 6,904,408 | B1 | 6/2005 | McCarthy et al. |
| 7,169,113 | B1 | 1/2007 | Young |
| 7,181,438 | B1 | 2/2007 | Szabo |
| 2001/0048439 | A1 | 12/2001 | Young |
| 2004/0210479 | A1 | 10/2004 | Perkowski et al. |
| 2005/0283395 | A1 | 12/2005 | Lesandrini et al. |
| 2006/0178908 | A1 | 8/2006 | Rappaport |
| 2006/0212350 | A1 | 9/2006 | Ellis et al. |
| 2007/0198353 | A1 | 8/2007 | Behringer et al. |
| 2008/0097854 | A1 | 4/2008 | Young |
| 2008/0147487 | A1 | 6/2008 | Hirshberg |

FOREIGN PATENT DOCUMENTS

| | | |
|---|---|---|
| KR | 10-2001-0008077 | 8/2002 |
| KR | 10-2003-0031809 | 12/2004 |
| KR | 10-2006-7026074 | 1/2007 |

OTHER PUBLICATIONS

Young, Charles et al., "Guideline: tracking the Commerical Viewer's Wandering Attention", *Journal of Advertising Research*—Jun./Jul. 1987, 15-22.

Page, Graham et al., "Cognitive Neuroscience, Marketing and Research", *Congress 2006*, 1-25.

Young, Charles E. et al., "Video Rhythms and Recall", *Journal of Advertising Research* 1989, 22-25.

Tulving, Endel, "Precis of Elements of episodic memory", *The Behavioral and Brain Sciences 7:2* 1984, 223-268.

* cited by examiner

½ Second

The consumer's eye is attracted to the message in the
boxes [with the words "my pet"] and
the dog at the top of the ad.

1 Second

The attention moves down from the store's logo (to the boxes with the "PetSmart" logo).

4 Seconds

Finally the consumer begins examining the prices of products featured on the sides [framing the center blocks].

PORTRAYAL OF HUMAN INFORMATION VISUALIZATION

CROSS-REFERENCE TO RELATED APPLICATIONS

This application is a continuation application of U.S. patent application Ser. No. 09/517,195, entitled "Portrayal of Human Information Visualization", filed on Mar. 2, 2000, which application is a continuation of International Application PCT/US98/18434, with an international filing date of Sep. 4, 1998, and which application also claims the benefit of the filing of U.S. Provisional Patent Application Ser. No. 60/057,973, entitled Method for Displaying How Humans Visually Process Information, filed on Sep. 5, 1997. The specifications and claims of all said applications are incorporated herein by reference.

BACKGROUND OF THE INVENTION

1. Field of the Invention (Technical Field)

The present invention relates to display of information concerning human information visualization, particularly of two-dimensional objects such as advertisements.

2. Background Art

In developing effective means to communicate with people using visual presentations, means for determining effectiveness of such presentations are required. In order to create effective advertisements, for example, one must have an effective means of judging the effects of the advertisement on the consumer. Preferably, such means must be easily and intuitively understood by decision makers at all levels.

Prior mechanisms for assessing information concerning consumer processing of visual information, of varying complexity, include U.S. Pat. No. 5,676,138, to Zawilinski, entitled "Emotional Response Analyzer System with Multimedia Display"; U.S. Pat. No. 5,465,729, to Bittman et al., entitled "Method and Apparatus for Biofeedback"; U.S. Pat. No. 5,331,969, to Silberstein, entitled "Equipment for Testing or Measuring Brain Activity"; U.S. Pat. No. 5,227,874, to Von Kohorn, entitled "Method for Measuring the Effectiveness of Stimuli On Decisions of Shoppers"; U.S. Pat. No. 5,052,401, to Sherwin, entitled "Product Detector for a Steady Visual Evoked Potential Stimulator and Product Detector"; U.S. Pat. No. 4,861,154, to Sherwin et al., entitled "Automated Visual Assessment System With Steady State Visual Evoked Potential Stimulator and Product Detector"; and U.S. Pat. No. 4,647,964, to Weinblatt, entitled "Technique for Testing Television Commercials".

None of the above patents discloses the technique of the present invention in displaying information about reaction to an image by breaking the image into matrix cells and varying transparency of cells depending on information gathered about that cell. None of the prior disclosures are believed to have the intuitive impact of the present invention, and therefore are unlikely to be as successful in providing accurate information to decision makers.

SUMMARY OF THE INVENTION

Disclosure of the Invention

The present invention is of an apparatus and method for displaying viewer reactions to a display object comprising: dividing the display object into a plurality of spatial regions; collecting viewer reactions to an exposure to the display object; correlating the viewer reactions with the spatial regions; and displaying the display object with an aspect of the display of each spatial region being a function of the viewer reactions for the region. In the preferred embodiment, the display object is divided into a matrix, with each spatial region being a cell of the matrix. Collecting is preferably by exposing a viewer, or a plurality of viewers, to the display object for a duration of between ¼ and 4 second, and most preferably a plurality of exposures to the display object are employed. The display object is displayed with the transparency (and/or color tingeing) of each spatial region being a function of the viewer reactions for the region. A static image (or images) may be displayed, or a motion picture sequence employed, preferably of a plurality of images corresponding to a plurality of viewer exposures to the display image.

A primary object of the present invention is to provide a straightforward means for displaying information collected about a display object's impact on viewers.

A primary advantage of the present invention is that it is intuitively understandable by decision makers at all levels.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

Best Modes for Carrying Out the Invention

The purpose of the present invention is to provide an intuitively appealing method for displaying diagnostic research data or information collected about how an audience or sample of research subjects processes and responds to visually complex display objects. Such a method aids decision makers in quickly seeing the strengths and weaknesses of different elements of a display object in terms of how well they elicit desired effects.

A "display object", for purposes of the specification and claims, is any visual stimulus represented or projected on a two-dimensional surface and designed to communicate a specific set of messages in order to elicit an intended response from viewers of that stimulus. Display objects include print advertisements, pages from catalogs, magazines or other printed publications, and screens from pages published electronically, as on the Internet or CD-ROMs. Display objects also include photographs or artistic renderings used as virtual representations of three dimensional communication spaces such as store environments, exhibition spaces, or street scenes (e.g., one cluttered with signage).

The present invention is designed to work with various manners of data collection that measure a human response to various parts of a display object. Two data collection methods are preferred, but others will be seen to be useful with the present invention by one skilled in the art.

The first preferred data collection approach makes use of controlled time exposures via a computerized interview. Each respondent is exposed to the display object on a computer screen for a sequence of measured time periods. For example, the respondent might be exposed to the test for three time exposures: ½ second, 1 second, and 4 seconds. After each exposure, the respondent is asked to record what he or she saw. The respondent may also be asked to indicate where exactly on the page or screen he or she saw items and that data is recorded on a grid. The information is then coded to determine how long it takes for viewers to register key elements such as a headline, a character, a package, a brand name, or the like. Depending on the purposes of the study, different time periods and a different number of exposures may be used. This method of data collection measures the order in which respondents take in or process the information contained in a display object.

The second preferred data collection approach is concerned with how people respond to the different parts of the display object. Response can refer to likeability or appeal, purchase interest, relevance, or some other measure of emotional or cognitive response. For this measurement, respondents are shown a copy of the display object with a grid or matrix superimposed over it and are asked to provide a rating of their level of response to each cell of the matrix.

Figure 1:
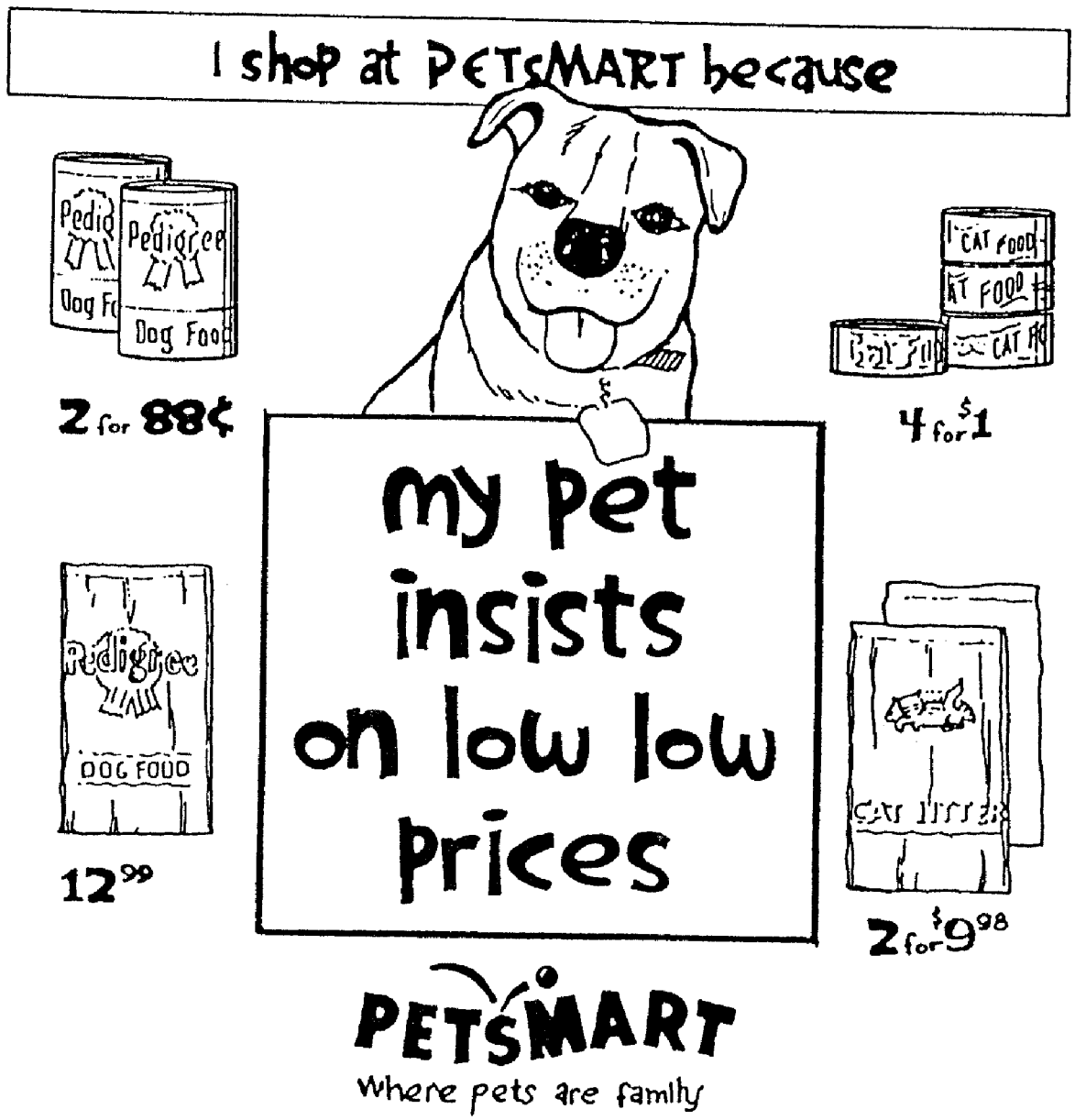
FIG. 1 illustrates a display object to be displayed according to the invention.

The invention is of a method of displaying information gathered about a display object, such as that of FIG. 1, divided into a grid. First, an opaque screen in the form of an n×m matrix is superimposed on a copy of the display object. Next, the research measurement associated with a particular cell of the matrix is used to determine the degree of transparency of the part of the screen covering that cell. For example, if after a ¼ second exposure, 30% of respondents indicated that they noticed a package in the part of the display object contained in cell 1×2, then the degree of transparency of the opaque screen covering cell 1×2 would be set to a value which is a function of 30%, such as the function x=x, which results in a 30% transparency. This adjustment is preferably performed for all cells in the matrix for each measurement taken.

Figure 2:
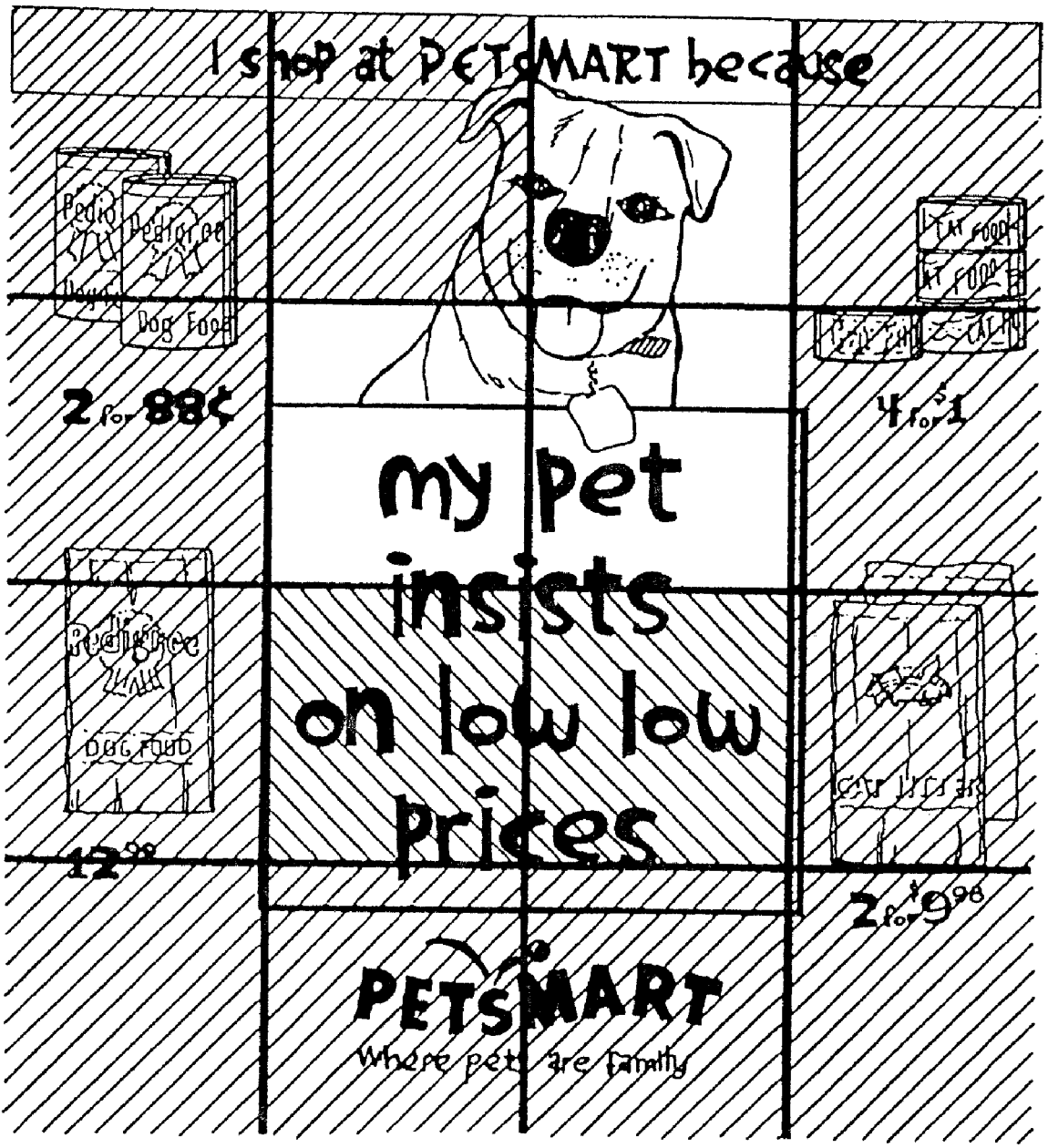
FIGS. 2-4 illustrate the display of the invention of viewer information collected about the display object of FIG. 1 at ½, 1, and 4 second exposures, respectively.
Figure 3:
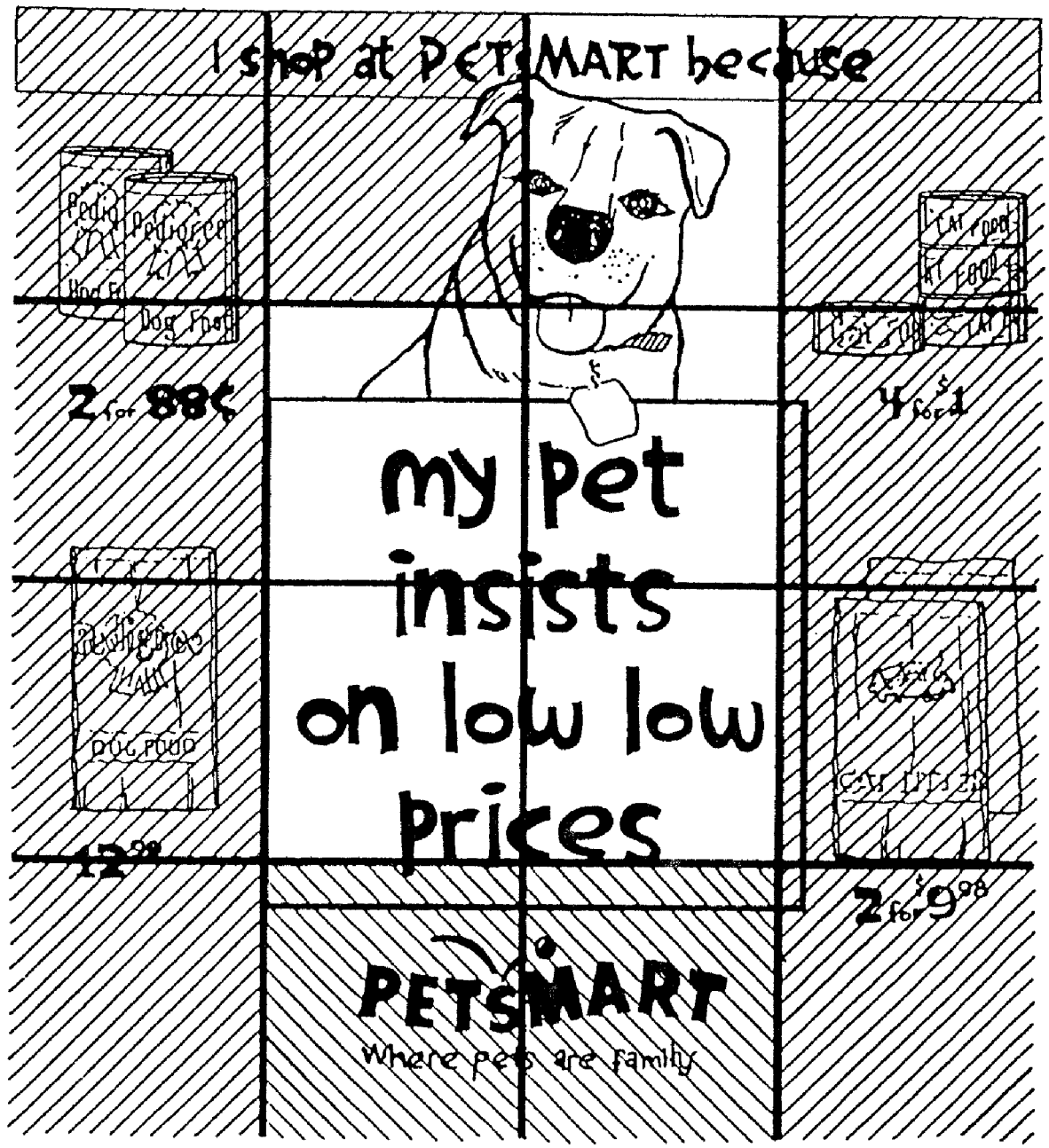
Figure 4:
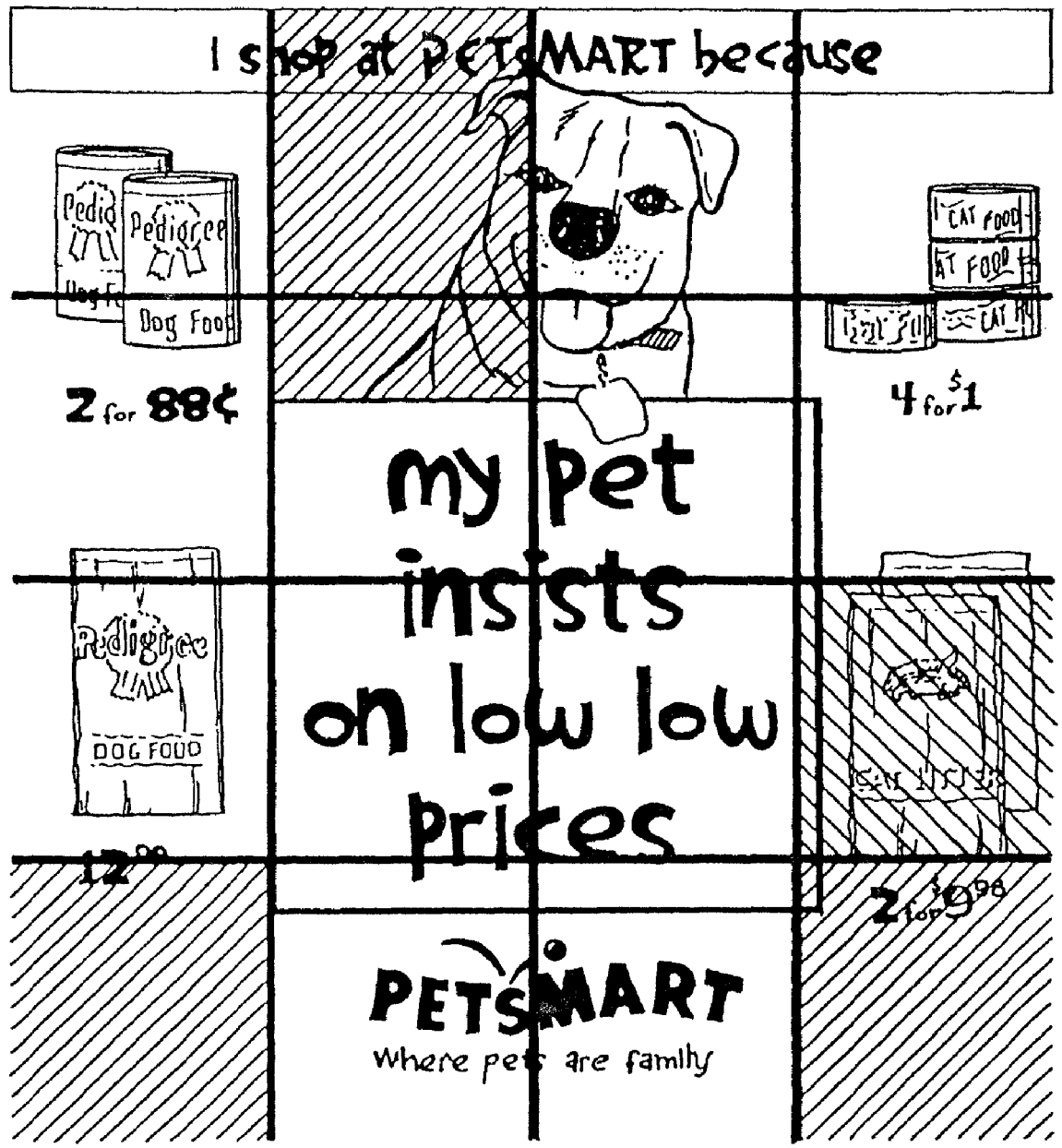

In order to display the sequence of viewer information processing, two types of display may be used. The first display presents all of the measurements collected simultaneously in a side-by-side arrangement of the different display screens associated with the timed exposures. An example of this type of display is shown in FIGS. 2-4. FIG. 2 shows that the consumer's eye at the ½ second mark is attracted to the message in the yellow box and the dog at the top of the display object. FIG. 3 shows that the attention at the 1-second mark moves down to the store's logo. FIG. 4 shows that at the 4-second mark the consumer begins examining the prices of products featured on the sides of the display object. A second display type is in the form of a movie that shows the progression of viewer attention in a more dynamic way, with a dramatic effect much like that of a photograph developing in the darkroom of viewer consciousness.

In order to display information about viewer response, a similar approach is used insofar as a semi-transparent screen divided into measurement cells is superimposed on the display object. In order to remind decision-makers that a different measurement is being referred to in the display, color may be used with the degree of color saturation indexed to the underlying measurement.

Figure 5:
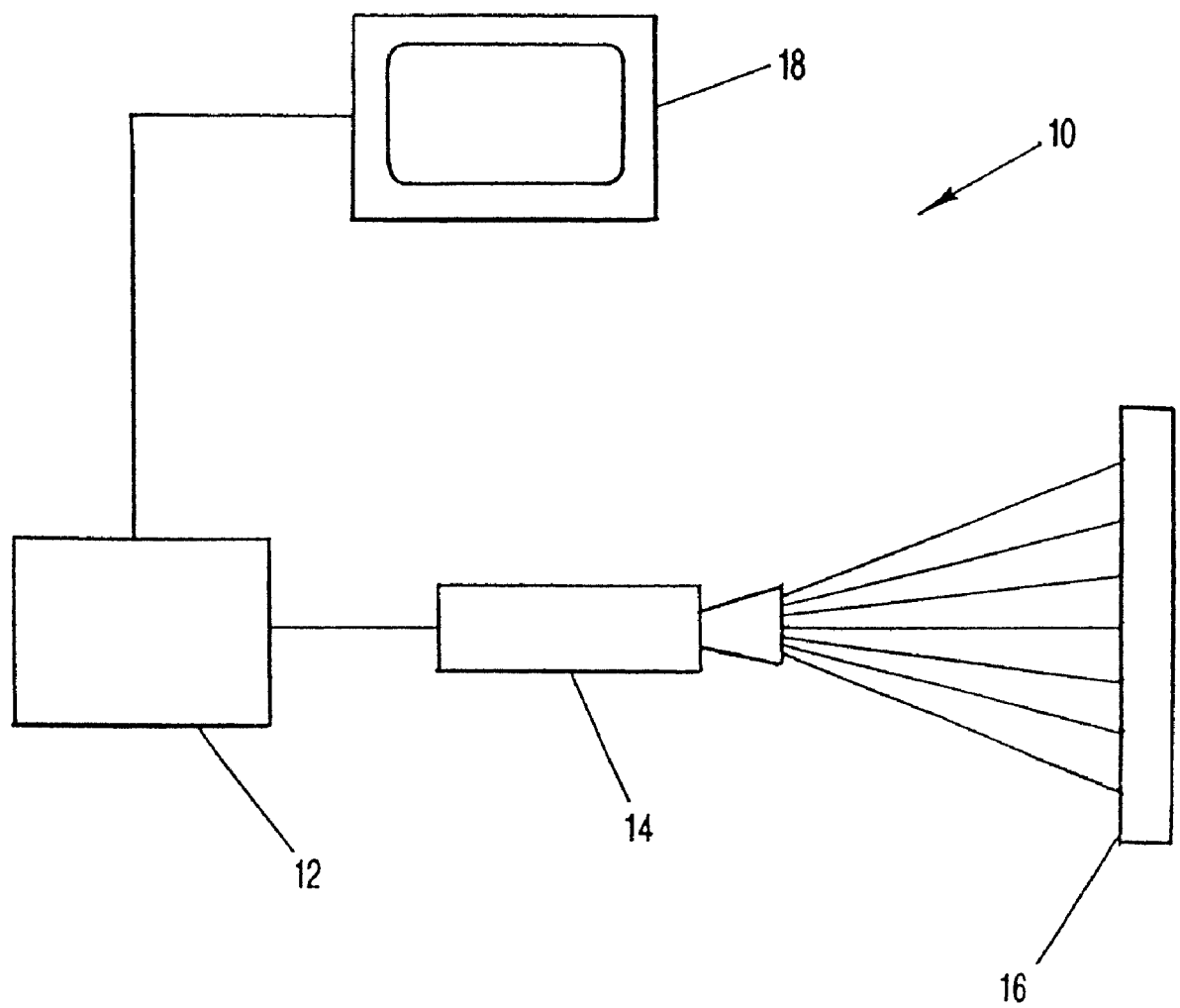
FIG. 5 is a schematic diagram of the preferred apparatus of the invention.

FIG. 5 illustrates the preferred embodiment of the apparatus of the invention 10. Personal computer 12, or like image processor, is used to receive and/or calculate the correlations between collected information from viewers and spatial regions of a display object designated by the user. The personal computer or image processor then places into video memory (or like storage) an appropriate image of the display object with spatial regions assigned different transparencies and/or color tingeing. Images according to the invention may then be displayed in any manner known to the art, such as on a display 18 or on surface 16 via projector 14 (such as a liquid-crystal device (LCD) projector).

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for analyzing viewer response to a still frame display object, the method comprising the steps of:

exposing a viewer to a still frame display object comprising a plurality of spatial regions on a computer screen for a first time period, each spatial region comprising only a portion of the entire spatial extent of the still frame display object;

asking the viewer which first spatial region of the still frame display object the viewer noticed;

exposing the viewer to the still frame display object on a computer screen for a second time period;

asking the viewer which second spatial region of the still frame display object the viewer noticed;

correlating the spatial regions with elements comprising the still frame display object;

displaying the order in which the elements were noticed by the viewer.

2. The method of claim 1 wherein the second time period is longer than the first time period.

3. The method of claim 1 wherein the first time period is selected from the group consisting of approximately ½ second and approximately 1 second.

4. The method of claim 1 wherein the second time period is selected from the group consisting of approximately 1 second and approximately 4 seconds.

5. The method of claim 1 wherein the exposing and asking steps are performed for a plurality of viewers.

6. The method of claim 5 further comprising the step of determining the number of viewers noticing a particular element after each time period.

7. The method of claim 6 wherein the displaying step comprises displaying which first element the largest number of viewers noticed after being exposed to the still frame display object for the first time period.

8. The method of claim 7 wherein the displaying step comprises displaying which second element the largest number of viewers noticed after being exposed to the still frame display object for the second time period.

9. The method of claim 6 wherein the displaying step comprises displaying one still frame display object for each time period, each still frame display object being modified to identify a quantity selected from the group consisting of the actual number of viewers noticing one or more of the elements and the relative number of viewers noticing one or more of the elements.

10. The method of claim 6 wherein the displaying step comprising displaying a movie showing the still frame display object modified in time to identify a quantity selected from the group consisting of the actual number of viewers noticing one or more of the elements and the relative number of viewers noticing one or more of the elements.

11. The method of claim 1 further comprising the step of receiving answers from the viewers using a computer system.

* * * * *